United States Patent
Brömster

(10) Patent No.: US 7,073,502 B2
(45) Date of Patent: Jul. 11, 2006

(54) MANUAL VENTILATION SYSTEM INCLUDING MANUAL BAG FILLING VALVE

(75) Inventor: Leif Brömster, Solna (SE)

(73) Assignee: Instrumentarium Corp., Helsinki (FI)

( * ) Notice: Subject to any disclaimer, the term of this patent is extended or adjusted under 35 U.S.C. 154(b) by 544 days.

(21) Appl. No.: 10/352,014

(22) Filed: Jan. 27, 2003

(65) Prior Publication Data

US 2004/0144385 A1 Jul. 29, 2004

(51) Int. Cl.
*A61M 16/00* (2006.01)

(52) U.S. Cl. .......................... 128/205.13; 128/205.24; 128/207.16

(58) Field of Classification Search ...................... None
See application file for complete search history.

(56) References Cited

U.S. PATENT DOCUMENTS

| | | | |
|---|---|---|---|
| 4,575,042 A | | 3/1986 | Grimland et al. |
| 4,702,242 A | | 10/1987 | Broddner et al. ...... 128/205.13 |
| 5,497,767 A | * | 3/1996 | Olsson et al. .......... 128/205.13 |
| 5,507,280 A | | 4/1996 | Henkin et al. |
| 6,131,571 A | * | 10/2000 | Lampotang et al. ... 128/204.21 |
| 6,148,816 A | | 11/2000 | Heinonen et al. ...... 128/205.24 |
| 6,318,366 B1 | | 11/2001 | Davenport |
| 6,672,300 B1 | * | 1/2004 | Grant .................... 128/204.26 |
| 6,718,978 B1 | * | 4/2004 | Emtell ................... 128/204.28 |

FOREIGN PATENT DOCUMENTS

EP 0 904 793 3/1999

OTHER PUBLICATIONS

"Automatic Ventilation of the Lungs", William W. Mushin, 1980, Blackwell Scientific Publications, Oxford 16610 XP002283333; pp. 579-583; Figures 49.1-49.2.

* cited by examiner

*Primary Examiner*—Glenn K. Dawson
(74) *Attorney, Agent, or Firm*—Andrus, Sceales, Starke & Sawall, LLP

(57) ABSTRACT

An open ventilation system for intensified breathing that includes both a manual ventilation system and an automatic ventilation system. A ventilation selection switch is positioned in the system prior to the patient circuit to select between the manual and automatic ventilation systems. The manual ventilation system includes a manual bag filling valve that controls the flow of inhalation gases from the ventilation selection switch to a manual bag. The manual bag filling valve includes a valve assembly that is movable between an open position and a closed position based on the difference in the forces created by the pressures of the manual bag and the inhalation gas.

17 Claims, 4 Drawing Sheets

MANUAL VENTILATION SYSTEM INCLUDING MANUAL BAG FILLING VALVE

BACKGROUND OF THE INVENTION

The present invention generally relates to ventilation system for use in intensified breathing. More specifically, the present invention relates to an open ventilation system for use wherever anesthesia is being delivered to a patient through an intravenous line where the ventilation system includes both an automatic ventilation system and a manual ventilation system.

Ventilators are currently used for intensifying the breathing of a patient whose own breathing activity for some reason is inadequate. Ventilators are typically applied to patients anesthetized and relaxed during surgery and to those in intensive care environments. A conventional ventilator provides a cyclic ventilation of the lungs at a rate set by an operator within the intensive care environment.

Presently, a ventilation system that includes a manual ventilation component is normally a rebreathing system, with a bellows in a chamber for use in both an automated and manual mode, a $CO_2$ absorber and a special valve called APL or Berner valve. All these components, including the manual bag, must be autoclavable.

Therefore, a need currently exists for a ventilation system that eliminates the use of a bellows, a $CO_2$ absorber, an APL or Berner valve and an autoclavable manual bag to reduce the number of components that must be autoclaved. Further, a need exists for an open ventilation system that includes both a manual ventilation system and an automatic ventilation system whose connection to the patient can be controlled by a selective valve outside of the patient circle. Further, a need exists for a ventilation system in which the converted gasses from the patient are prevented from going back into the manual bag, such that the manual bag does not need to be autoclaved.

SUMMARY OF THE INVENTION

The present invention is directed to a ventilation system for use in intensified breathing, and particularly for use wherever anesthesia is being delivered to a patient through an intravenous line.

The ventilation system of the present invention includes both an automatic ventilation system and a manual ventilation system that can be alternatively selected by an operator to control the source of inhalation gases being supplied to a patient. The automatic ventilation system includes an automated ventilator for providing the automated cyclic ventilation of the patient's lung with inhalation gas when the automatic ventilation system is selected. Likewise, the manual ventilation system includes a manual bag that can be repeatedly compressed and released by an operator to provide a cyclic supply of inhalation gases to the patient.

The ventilation system includes a ventilation selection switch that allows the operator to control the supply of inhalation gases to the patient from either the automatic ventilation system or the manual ventilation system. The ventilation selection switch is positioned out of the manual ventilation system and thus is isolated from the patient's circuit and does not need to be autoclaved.

The ventilation selection switch includes an input from a compressed gas mixer and an input from the automatic ventilation system. When the ventilation selection switch is in a manual position, the inhalation gas from the mixer is supplied to an inflow conduit of the manual ventilation system. When the ventilation selection switch is in the automatic position, the output flow from the ventilator is supplied to an inhalation conduit of the patient circuit.

The manual ventilation system of the present invention includes a manual bag filling valve positioned between the inflow conduit coupled to the ventilation selection switch and the manual bag. The manual bag filling valve includes a valve assembly that allows the manual bag filling valve to move between an open position and a closed position. When the valve assembly of the manual bag filling valve is in an open position, inhalation gas is supplied to the manual bag for filling the manual bag. When the valve assembly of the manual bag filling valve is in the closed position, no further inhalation gas can flow into the manual bag.

The manual bag filling valve is configured such that the movement of the valve assembly is dictated by a pressure comparison between the inhalation gas and the pressure contained within the manual bag. If the pressure within the manual bag exceeds the pressure of the inhalation gas, the valve assembly is closed since the manual bag is fully inflated. If the pressure within the manual bag is below the pressure of the inhalation gas, the valve assembly moves to an open position and the manual bag is inflated. An adjustable bias spring is positioned to act in combination with the pressure in the manual bag to allow the operator further control of the movement of the valve assembly between the open and closed positions.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings.

DETAILED DESCRIPTION OF THE INVENTION

Figure 1:
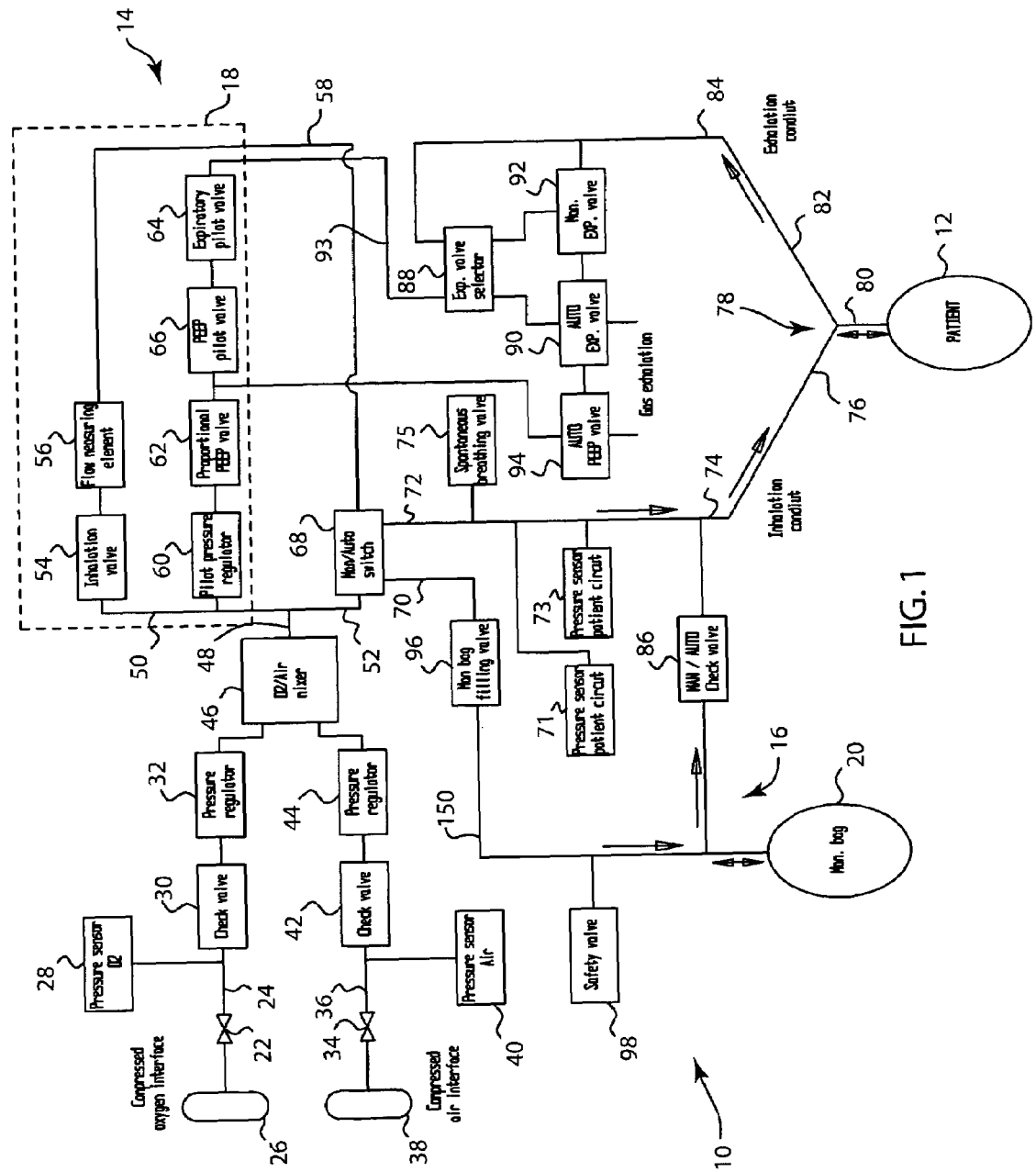
FIG. 1 illustrates an operational block diagram of a ventilation system of the present invention including a manual ventilation system and an automatic ventilation system for use in an intensive care environment.

A ventilation system 10 is shown in FIG. 1 for providing an inhalation gas to a patient 12 for use in intensified breathing. The ventilation system 10 of the present invention is particularly useful wherever the patient 12 is receiving intravenous anesthesia.

The ventilation system 10 generally includes an automatic ventilation system 14 and a manual ventilation system 16 that can be alternatively selected by an operator to provide inhalation gas to the patient. The automatic ventilation system 14 generally includes an automated ventilator 18, as shown in dashed lines in FIG. 1. The manual ventilation system 16 is centered around a manual bag 20 that can be repeatedly compressed and released by an operator to control the flow of inhalation gas to the patient 12. Further details of both the automatic ventilation system 14 and the manual ventilation system 16 will be described in detail below.

The ventilation system 10 shown in FIG. 1 includes a compressed oxygen interface 22, including a compressed oxygen conduit 24 connected to a compressed oxygen tank 26. Coupled to the compressed oxygen conduit 24 is an oxygen pressure sensor 28, a check valve 30 and a pressure regulator 32. The pressure regulator 32 is used to provide a constant level of pressure to a mixer 46.

In addition to the compressed oxygen branch, the ventilation system includes a compressed air interface 34, including a compressed air conduit 36. The compressed air conduit 36 is coupled to a compressed air tank 38 and includes an air pressure sensor 40 for monitoring the pressure of air within the compressed air conduit 36. The conduit 36 includes a check valve 42 and a pressure regulator 44 for providing a constant level of pressure to the mixer 46.

As illustrated in FIG. 1, both the compressed oxygen conduit 24 and the compressed air conduit 36 are coupled to the mixer 46 that can be operated by a control unit to control the blend of gas within the gas mixture conduit 48. The blend of gases in the conduit 48 is eventually directed to the patient 12 as the inhalation gas.

As illustrated in FIG. 1, the gas mixer conduit 48 is coupled to both a ventilator inlet conduit 50 that leads into the automatic ventilation system 14 and a manual ventilation conduit 52 that selectively supplies the mixed gases to the manual ventilation system 16.

The ventilator 18 of the automatic ventilation system 14 is a common component and includes an inhalation valve 54 and a flow measuring element 56. The flow of mixed, inhalation gas from the ventilator 18 exits through an automatic ventilator outlet conduit 58. Further, the ventilator 18 includes a pilot pressure regulator 60, and a proportional PEEP valve 62 coupled to the inlet conduit 50 to control the pressure to the auto PEEP valve 94. An expiratory pilot valve 64 and a PEEP pilot valve 66 are included in the ventilator 18 in a conventional manner.

The ventilation system 10 of the present invention includes a ventilation selection switch 68 positioned between the manual ventilation conduit 52 and the automatic ventilator outlet conduit 58. The ventilation selection switch 68 is operable to allow an operator to select either the automatic ventilation system 14 or the manual ventilation system 16 to supply the inhalation gases to the patient, as desired. When the ventilation selection switch 68 is in a manual position, inhalation gases from the manual ventilation conduit 52 are allowed to pass through to the inflow conduit 70 of the manual ventilation system 16.

When the ventilation selection switch 68 is in the automatic position, the flow of gases from the ventilator 18 contained within the automatic ventilator outlet conduit 58 pass through to the automatic outflow conduit 72. The automatic ventilator outflow conduit 72 includes a pair of pressure sensors 71 and 73 that monitor the pressure of gas flowing through the conduit 72 and a spontaneous breathing valve 75.

Both the inflow conduit 70 of the manual ventilation system 16 and the automatic outflow conduit 72 direct a flow of inhalation gases into an inhalation conduit 74 that is directly coupled to the inlet branch 76 of a Y-piece 78. The Y-piece 78 includes a patient branch 80 and an outlet branch 82, as is conventional.

The outlet branch 82 of the Y-piece 78 is coupled to an exhalation conduit 84 to direct the flow of expired gases from the patient for venting to atmosphere. A check valve 86 prevents the reverse flow of gases back into the manual and automatic ventilation systems.

The exhalation conduit 84 leads to an expiration valve selector 88. The valve selector 88 is coupled to both an automatic ventilation system expiration valve 90 and a manual ventilation system expiration valve 92 which allow expired gases to flow to atmosphere. The valve selector 88 is a pneumatically controlled valve that receives a control pressure along conduit 93. When the selector 88 is in the manual mode, the conduit to the valve 90 is open. The conduit to valve 92 is open when the selector 88 is in the auto mode. Additionally, a PEEP valve 94 allows gas to flow to atmosphere from the ventilator 18, as illustrated.

As illustrated in FIG. 1, the manual ventilation system 16 includes a manual bag filling valve 96 positioned between the inflow conduit 70 and the manual bag 20. The manual bag filling valve 96 controls the flow of inhalation gas into the manual bag when the manual bag 20 is not fully inflated and aids in directing the flow of inhalation gases from the manual bag 20 into the inhalation conduit 74 when the manual bag 20 is being compressed. A safety valve 98 is positioned to help control the pressure of gas within the manual bag 20, as will be described in greater detail below.

Figure 2A:
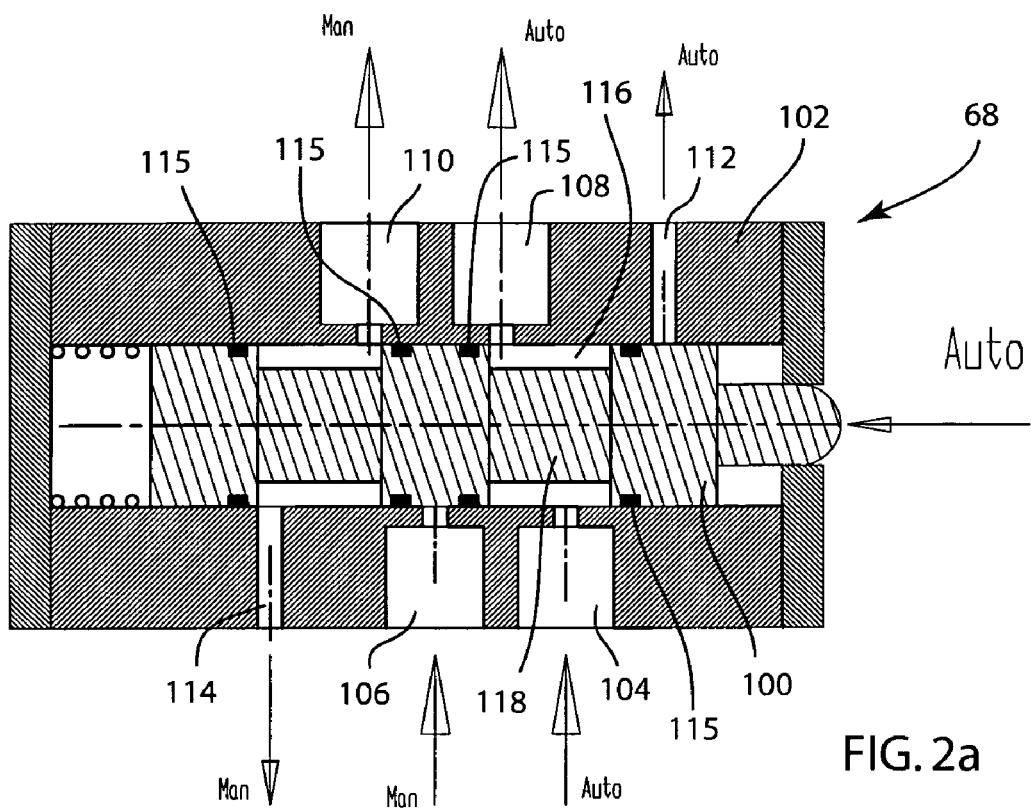
FIG. 2a is a cross-section of a ventilation selection switch in an automatic position to connect the automatic ventilation system to a patient.
Figure 2B:
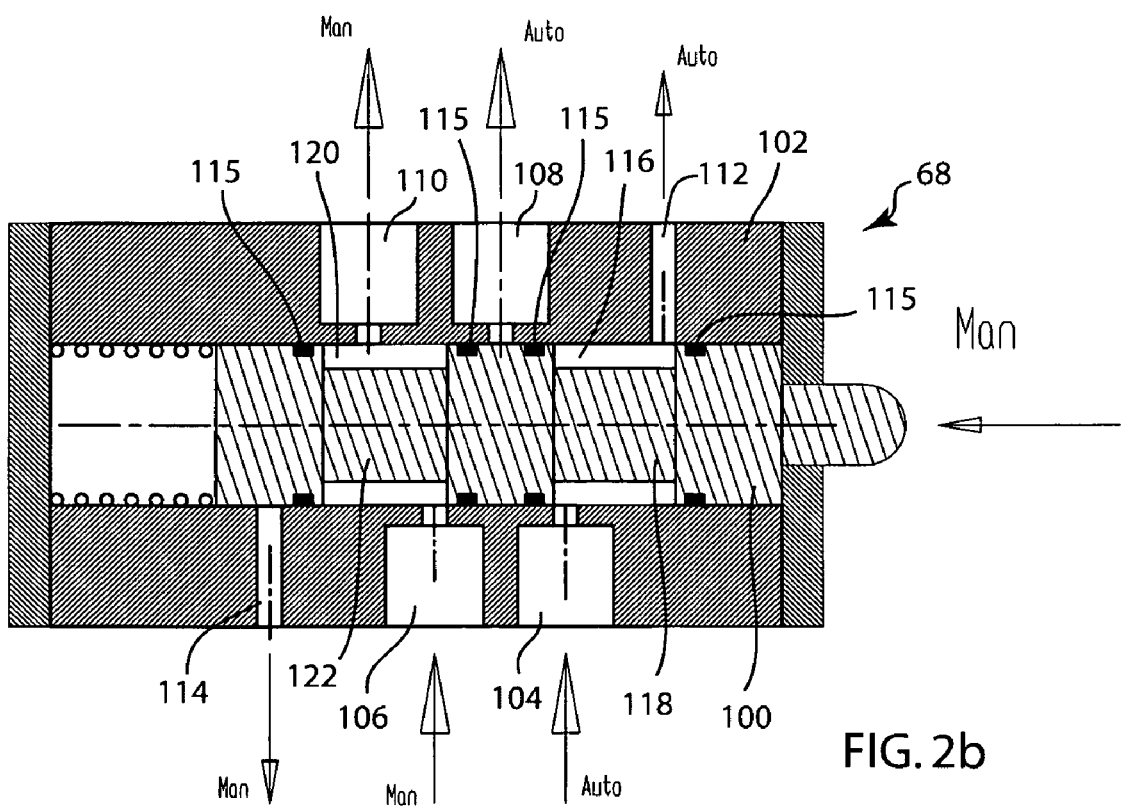
FIG. 2b is a cross-section of the ventilation selection switch in a manual position to connect the manual ventilation system to the patient.

Referring now to FIGS. 2*a* and 2*b*, thereshown is the detailed operation and configuration of the ventilation selection switch 68. The ventilation selection switch 68 includes a plunger 100 that is movable between the automatic position shown in FIG. 2*a* and the manual position shown in FIG. 2*b*. The plunger 100 is movable within a stationary body 102 having a plurality of passageways formed therein. Specifically, the main body 102 includes an automatic inlet port 104, a manual inlet port 106, an automatic outlet port 108 and a manual outlet port 110. Further, the body 102 includes an automatic vent port 112 and a manual vent port 114.

As can be understood by viewing FIG. 1 in combination with FIG. 2*a*, the automatic inlet port 104 receives the automatic ventilator outlet conduit 58 while the manual input port 106 receives the flow of inhalation gases from the manual ventilation conduit 52. The automatic outlet port 108 is coupled to the automatic outflow conduit 72, while the manual outlet port 110 is in communication with the inflow conduit 70.

Referring now to FIG. 2*a*, when the selection switch 68 is in the automatic position as illustrated, the automatic inlet port 104 is in fluid communication with the automatic outlet port 108 through an annular passageway 116 formed around a section 118 of the plunger 100. Thus, the flow of inhalation gases from the automatic ventilator conduit 58 is allowed to flow into the automatic outflow conduit 72 as illustrated in FIG. 1. Referring back to FIG. 2*a*, if a flow of inhalation gas is present at the manual inlet port 106, this flow of gases is vented to atmosphere through the manual vent port 114. A series of sealing members 115 prevent the undesired flow of gas between the plunger 100 and the body 102.

Referring now to FIG. 2*b*, when the plunger 100 is in the manual position as illustrated, the manual input port 106 is in communication with the manual outlet port 110 through an annular passageway 120 formed around a section 122 of the plunger 100. Thus, when the plunger 100 is in the manual position, the flow of inhalation gases can flow from the manual ventilation conduit 52 to the inflow conduit 70 as illustrated in FIG. 1.

Referring back to FIG. 2*b*, when the plunger is in the manual position, any flow of gas entering into the automatic inlet port 104 flows through the annular passageway 116 and out of the automatic vent passageway 112. Thus, if the ventilation selection switch 68 is in a manual position and flow is received from the automatic ventilation system 114, the switch 68 will be able to vent the undesired gas flow to atmosphere.

Figure 3A:
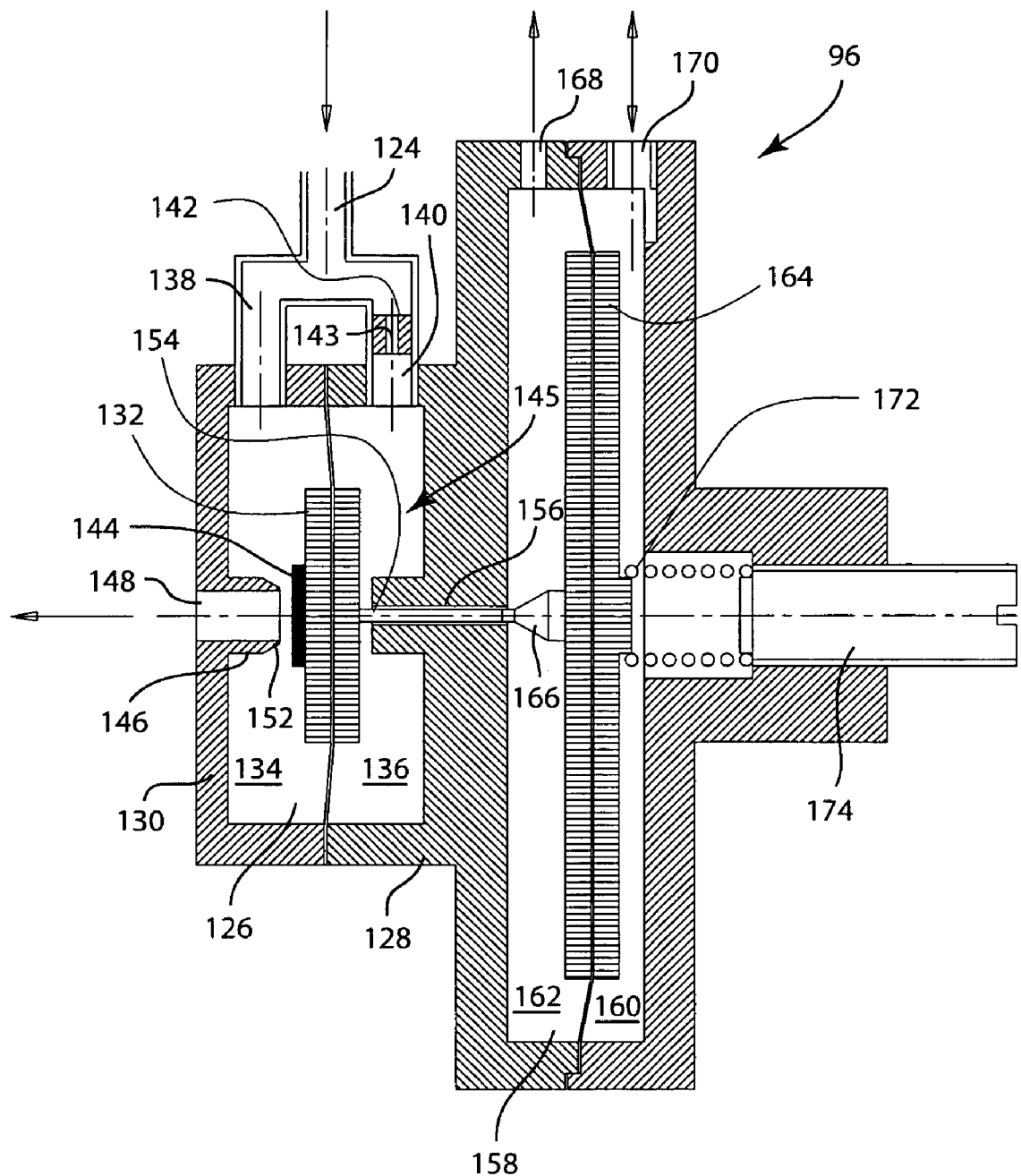
FIG. 3a is a cross-section view of a manual bag filling valve of the present invention in an open position.
Figure 3B:
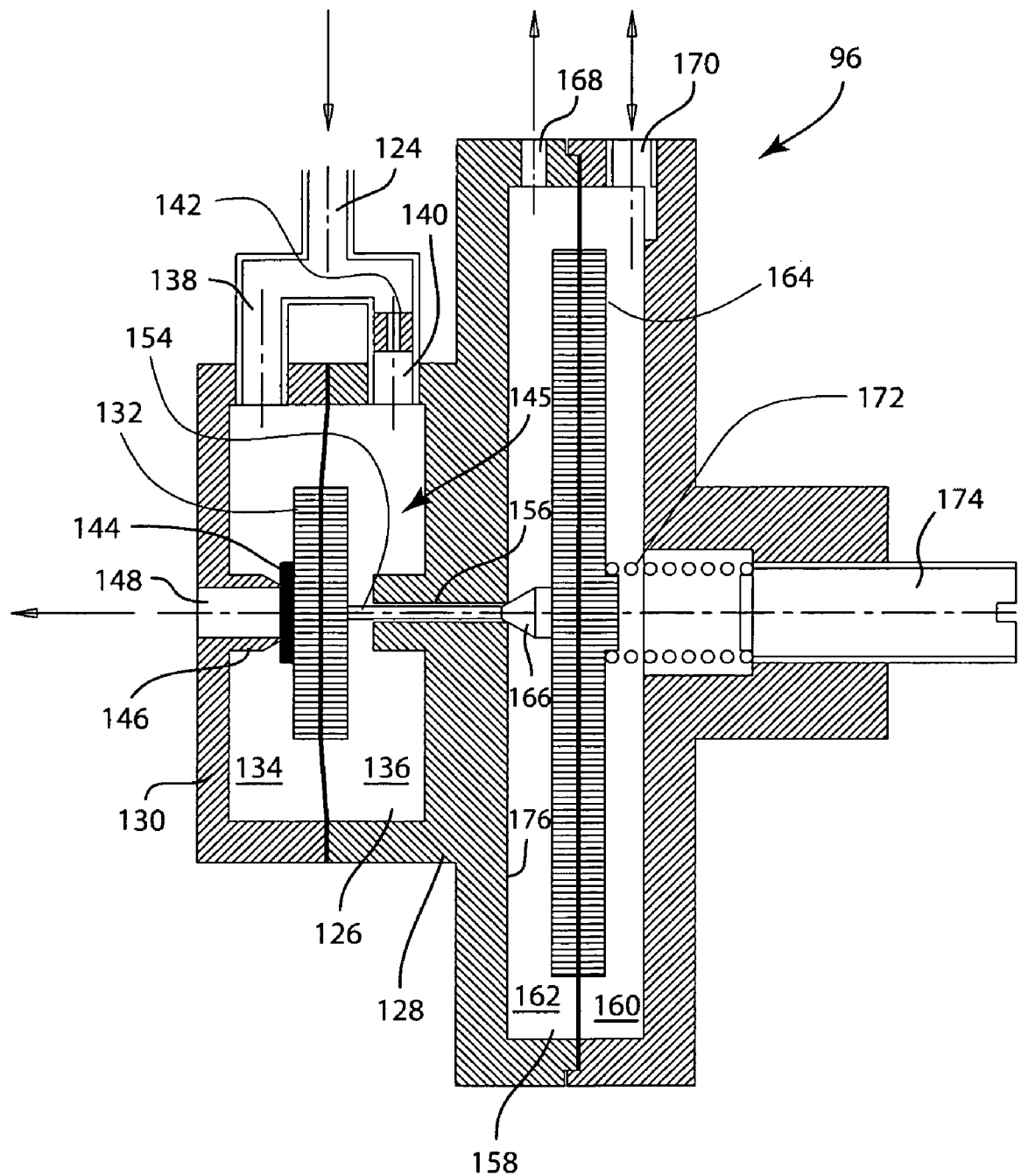
FIG. 3b is a cross-section view of the manual bag filling valve in a closed position.

Referring now to FIGS. 3a and 3b, thereshown is the detailed construction of the manual bag filling valve 96 used in the manual ventilation system 16 of the present invention. The manual bag filling valve 96 includes an inlet port 124 that is configured to receive the flow of inhalation gas from the ventilation selection switch 68 through the inflow conduit 70. The inflow conduit 70 is connected directly to the inlet port 124 and provides a flow of inhalation gas to the manual bag filling valve 96 when the selection switch 68 is in the manual position.

The inlet port 124 directs the flow of inhalation gas into an open cavity 126 defined by the main valve body 128 and an outer wall 130. The open cavity 126 is divided by a diaphragm 132 into a pair of pressure cavities 134 and 136. The first pressure cavity 134 is in communication with the inlet port 134 through a first branch 138, while the second pressure cavity 136 is in communication with the inlet port 124 through a second branch 140. A flow restrictor 142 having a reduced diameter center passageway 143 is positioned within the second branch 140 to restrict the rate at which the pressure cavity 136 fills as compared to the pressure cavity 134. Thus, when inhalation gases are present at the inlet port 124, the inhalation gases flow more quickly through the first branch 138 into the pressure cavity 134.

When a valve assembly 145 of the manual bag filling valve 96 is in the closed position of FIG. 3b, a seal member 144 is pressed into contact with an internal annular wall 146 that defines an outlet 148 of the manual bag filling valve 96. The outlet 148 is coupled to the manual bag 20 through a conduit 150, as illustrated in FIG. 1. As can be understood in FIG. 3a, when the valve assembly 145 of manual bag filling valve 96 is in an open position, the seal member 144 is spaced from the inner end 152 of the wall 146 to allow the inhalation gases within the pressure cavity 134 to flow out of the outlet 148. Likewise, when the valve assembly 145 of the manual bag filling valve 96 is in the closed position of FIG. 3b, the interaction between the seal member 144 and the inner wall 146 prevents the flow of inhalation gases out through the outlet 148. The movement of the valve assembly 145 between the open and closed positions will be described in greater detail below.

Referring back to FIG. 3a, the valve assembly 145 includes the diaphragm 132 connected to a valve stem 154 that extends through an internal passageway 156 formed in the valve body 128. The internal passageway 156 is in pressure communication with a second internal cavity 158. The second internal cavity 158 is divided into a first pressure cavity 160 and a second pressure cavity 162 by a second diaphragm 164. The second diaphragm 164 of the valve assembly 145 is coupled to the valve stem 154 by a conical sealing member 166. The conical sealing member 166 is movable between an open position shown in FIG. 3a and a closed position shown in FIG. 3b. When the conical sealing member 166 is in the closed position, gases are unable to flow between the pressure cavity 136 and the pressure cavity 162. However, when the conical sealing member 166 is spaced from the inlet to the internal passageway 156, gases can flow from the pressure cavity 136 to the pressure cavity 162. The pressure cavity 162 is connected to atmospheric pressure through an outlet port 168 to permit the venting of pressure within the valve 96 to atmosphere.

As illustrated in FIGS. 3a and 3b, the first pressure cavity 160 includes an inlet port 170. In the embodiment of the invention illustrated, the inlet port 170 is in pressure communication with the manual bag 20. Thus, the pressure within the first pressure cavity 160 mirrors the pressure within the manual bag 20.

As illustrated in FIG. 3a, the side of the second diaphragm 164 in communication with the first pressure cavity 160 is acted upon by a bias spring 172. The bias spring 172 exerts a bias force on the second diaphragm 164 to urge the conical sealing member 166 and the seal member 174 toward their closed positions. The amount of bias force exerted by the bias spring 174 is controlled by an adjustment member 174 that is movable along its longitudinal axis to either compress the bias spring 172 or allow the bias spring 172 to extend.

Referring now to FIGS. 3a and 3b, the operation of the manual bag filling valve 96 will be described in detail. Initially, assume that the manual bag 20 is completely filled with inhalation gases and the manual ventilation system 16 is ready to be operated. When the manual bag 20 is filled, the pressure within the manual bag 20 is communicated to the first pressure cavity 160 through the inlet port 170. Typically, the pressure within the manual bag 20 is in the range of 0.5–20 cm of water. The combination of the pressure within the first pressure cavity 160 and the bias force created by the bias spring 172 moves the second diaphragm 164 into the position shown in FIG. 3b. In the position shown in FIG. 3b, the conical sealing member 168 contacts the inner wall 176 to prevent gas flow between the cavity 136 and the cavity 162. At the same time, the seal member 144 is pressed into contact with the internal annular wall 144 to prevent the flow of gases out of the outlet 148. Thus, no additional inhalation gases flow to the manual bag 20 through the conduit 150 shown in FIG. 1.

As illustrated in FIG. 3b, when the first diaphragm 132 is in the closed position shown, the pressure cavity 134 is at the same pressure as the flow of inhalation gases from the ventilation selection switch 68 through the inflow conduit and the inlet port 124. Typically, the pressure of the inhalation gases is at approximately 1–3 bar. Since the force created by the pressure within the first pressure cavity 160 in combination with the bias force from the bias spring 172 is greater than the force created by the pressure within the pressure cavity 134, the seal member 144 remains in its closed position.

Once the manual bag 20 has been compressed and the inhalation gases delivered to the patient 12, the pressure within the manual bag falls to a negligible value, which is communicated to the inlet port 170. Since the force created by the pressure within the first pressure cavity 160 is well below the force created by the pressure within the pressure cavity 134, the first diaphragm 132 and the second diaphragm 164 move to the open position illustrated in FIG. 3a. In this open position, the flow of inhalation gas passes through the inlet port 124 and the first branch 138, into the pressure cavity 134 and out of the outlet 148. The outlet 148 is coupled to the manual bag 20 such that the manual bag begins to refill. At the same time the manual bag is refilling, the gases within the pressure cavity 136 are vented to atmosphere through the internal passageway 156, the second pressure cavity 162 and the outlet port 168.

Inhalation gases continue to flow out of the outlet 148 until the pressure within the manual bag is sufficient such that the pressure within the first pressure cavity 160 combined with the bias force from the spring 172 is sufficient to move the valve back to the closed position shown in FIG. 3b. This process continues for each compression and filling of the manual bag.

As can be understood by the foregoing description, the bias spring 172 allows the user to control the pressure within the manual bag 20 since the bias spring 172 functions to control the flow of inhalation gases through the outlet 148.

Various alternatives and embodiments are contemplated as being within the scope of the following claims particularly pointing out and distinctly claiming the subject matter regarded as the invention.

I claim:

1. An open ventilation system for intensified breathing, the ventilation system comprising:
   at least one compressed gas interface for providing a supply of inhalation gas for breathing by a patient;
   an automatic ventilation system positioned to receive inhalation gas from the compressed gas interface for providing an automated cyclic ventilation of the patient's lungs with the inhalation gas;
   a manual ventilation system positioned to receive inhalation gas from the compressed gas interface for the manual cyclic ventilation of the patient's lungs with inhalation gas;
   an inhalation conduit positioned to supply inhalation gas to the patient from either of the automatic ventilation system and the manual ventilation system;
   a ventilation selection switch operable to selectively connect either of the automated ventilation system and the manual ventilation system to the inhalation conduit;
   a manual bag arranged in the manual ventilation system to supply inhalation gas to the inhalation conduit upon the repeated manual compression and release of the manual bag;
   a manual bag filling valve arranged in the manual ventilation system between the ventilation selection switch and the manual bag to control the supply of inhalation gas to the manual bag, the manual bag filling valve being in a closed position to prevent inhalation gas from being supplied to the manual bag, the manual bag filling valve being in an open position to supply inhalation gas to the manual bag; and
   an exhalation conduit for receiving exhaled gases expired from the patient.

2. The ventilation system of claim 1 wherein the manual bag filling valve includes a valve assembly positioned between an inhalation gas inlet and an inhalation gas outlet, the inhalation gas outlet coupled to the manual bag.

3. The ventilation system of claim 2 wherein the position of the valve assembly is controlled by the difference in forces between the force created by the pressure in the manual bag and the force created by the pressure of the inhalation gas.

4. The ventilation system of claim 3 wherein the valve assembly includes a first diaphragm having a first side in pressure communication with the inhalation gas and a second diaphragm having a first side in pressure communication with the manual bag, wherein when the force created by the pressure on the first diaphragm is greater than the force created by the pressure on the second diaphragm, the valve assembly moves to the open position.

5. The ventilation system of claim 4 wherein the second diaphragm includes a second side in pressure communication with atmospheric pressure.

6. The ventilation system of claim 5 wherein the valve assembly further comprises a bias spring in contact with the first side of the second diaphragm.

7. The ventilation system of claim 6 wherein the first diaphragm includes a second side in pressure communication with the inhalation gas through a flow restrictor.

8. The ventilation system of claim 6 wherein the bias spring is adjustable to exert a selected bias force on the first side of the second diaphragm such that when the combination of the bias force and the force created by the pressure of the manual bag exceeds the force created by the pressure of the inhalation gas, the valve assembly is moved to a closed position.

9. The ventilation system of claim 1 further comprising a check valve positioned between the manual bag and the inhalation conduit to prevent the flow of exhalation gases from the patient to the manual bag.

10. The ventilation system of claim 1 wherein the ventilation selection switch comprises:
    a manual input port coupled to the compressed gas interface;
    an automatic input port coupled to the automatic ventilation system;
    a manual output port coupled to the manual ventilation system;
    an automatic outlet port coupled to the patient conduit; and
    a plunger movable between an automatic position and a manual position, wherein when the plunger is in the automatic position, the ventilation selection switch permits the flow of gas from the automatic input port to the automatic outlet port and wherein when the plunger is in the manual position, the ventilation selector switch allows gas to flow from the manual input port to the manual output port.

11. The ventilation system of claim 10 wherein the ventilation selector switch further includes a vent port, the vent port being in communication with the automatic input port when the plunger is in the manual position.

12. An open ventilation system for intensified breathing, the ventilation system comprising:
    at least one compressed gas interface for providing a supply of inhalation gas for breathing by a patient;
    an automatic ventilation system positioned to receive inhalation gas from the compressed gas interface for providing an automated cyclic ventilation of the patient's lungs with the inhalation gas, the automatic ventilation system including an outlet conduit;
    a manual ventilation system positioned to receive inhalation gas from the compressed gas interface for the manual cyclic ventilation of the patient's lungs with inhalation gas, the manual ventilation system including an inflow conduit and a manual outlet conduit;
    an inhalation conduit positioned to selectively supply inhalation gas to the patient from either the outlet conduit of the automatic ventilation system or the outlet conduit of the manual ventilation system;
    a ventilation selection switch operable to selectively connect either the outlet conduit of the automated ventilation system to the inhalation conduit or the compressed gas interface to the inflow conduit of the manual ventilation system;
    a manual bag arranged in the manual ventilation system to selectively supply inhalation gas to the inhalation conduit upon the repeated manual compression and expansion of the manual bag;
    a manual bag filling valve arranged in the manual ventilation system between the inflow conduit and the manual bag to control the supply of inhalation gas to the manual bag, the manual bag filling valve being movable to a closed position to prevent inhalation gas from being supplied to the manual bag and the manual bag filling valve being movable to an open position to supply inhalation gas to the manual bag, wherein the movement of the manual bag filling valve between the open position and the closed position is controlled by the pressure difference between the manual bag and the inhalation gas; and an exhalation conduit for receiving exhaled gases expired from the patient.

13. The ventilation system of claim 12 wherein the manual bag filling valve includes a valve assembly positioned between an inhalation gas inlet and an inhalation gas outlet, the inhalation gas outlet being coupled to the manual bag, wherein the position of the valve assembly is controlled by the difference between the force created by the pressure of the inhalation gas relative to the force created by the pressure within the manual bag.

14. The ventilation system of claim 13 wherein the valve assembly includes a first diaphragm having a first side in pressure communication with the inhalation gas and a second diaphragm having a first side in pressure communication with the manual bag, wherein when the force created by the pressure of the inhalation gas is greater than the force created by the pressure of the manual bag, the valve assembly moves to the open position.

15. The ventilation system of claim 14 wherein the valve assembly further comprises a bias spring positioned to exert a bias force on the valve assembly in combination with the force created by the pressure of the manual bag, wherein the valve assembly moves to the closed position when the combination of the bias force and the force created by the pressure of the manual bag exceeds the force created by the pressure of the inhalation gas.

16. The ventilation system of claim 15 wherein the bias force is adjustable.

17. The ventilation system of claim 12 wherein the ventilation selection switch comprises:

the manual input port coupled to the compressed gas interface;

an automatic input port coupled to the outlet conduit of the automatic ventilation system;

a manual output port coupled to the inflow conduit of the manual ventilation system;

an automatic outlet port coupled to the patient conduit; and a plunger movable between an automatic position and a manual position, wherein when the plunger in the automatic position, the ventilation selection switch permits the flow of gas from the automatic input port to the automatic outlet port and wherein when the valve member is in the manual position, the ventilation selector switch allows gas to flow from the manual input port to the manual port.

* * * * *